US009481477B2

(12) United States Patent
Kjar

(10) Patent No.: US 9,481,477 B2
(45) Date of Patent: Nov. 1, 2016

(54) FLUID MANIFOLD SYSTEM WITH ROTATABLE PORT ASSEMBLY

(71) Applicant: HyClone Laboratories, Inc., Logan, UT (US)

(72) Inventor: Steven R. Kjar, Logan, UT (US)

(73) Assignee: Life Technologies Corporation, Carlsbad, CA (US)

( * ) Notice: Subject to any disclaimer, the term of this patent is extended or adjusted under 35 U.S.C. 154(b) by 280 days.

(21) Appl. No.: 13/970,387

(22) Filed: Aug. 19, 2013

(65) Prior Publication Data

US 2014/0076454 A1 Mar. 20, 2014

Related U.S. Application Data

(60) Provisional application No. 61/701,832, filed on Sep. 17, 2012.

(51) Int. Cl.
*B65B 3/28* (2006.01)
*A61M 39/22* (2006.01)
*B65B 3/00* (2006.01)
(Continued)

(52) U.S. Cl.
CPC .............. *B65B 3/28* (2013.01); *A61M 39/223* (2013.01); *B65B 3/003* (2013.01); *C12M 23/40* (2013.01); *F16K 11/0853* (2013.01); *B65B 3/30* (2013.01); *B65B 3/36* (2013.01); *B65B 39/003* (2013.01); *Y10T 137/86558* (2015.04)

(58) Field of Classification Search
CPC ................... Y10T 137/86558; A61M 39/223; B65B 3/003; B65B 3/28; B65B 3/30; B65B 3/36; B65B 39/003; F16K 11/0853

USPC .............. 141/1, 234–250, 256, 259, 260, 141/268–270; 137/597, 625.18
See application file for complete search history.

(56) References Cited

U.S. PATENT DOCUMENTS 250,500 A * 12/1881 Chewning ................. B67C 3/22
141/129
702,406 A * 6/1902 Cody ..................... B60K 15/00
137/256

(Continued)

FOREIGN PATENT DOCUMENTS

DE 807216 6/1951
GB 1 549 100 7/1979

OTHER PUBLICATIONS

Partial Search Report dated Nov. 19, 2013, issued in PCT Application No. PCT/US2013/055618, filed Aug. 19, 2013.
(Continued)

*Primary Examiner* — Mark A Laurenzi
*Assistant Examiner* — Andrew Schmid
(74) *Attorney, Agent, or Firm* — Workman Nydegger

(57) ABSTRACT

A fluid manifold system includes a manifold port assembly having a housing with an inlet port and a plurality of outlet ports formed thereon and a carousel having a plurality of spaced apart fluid paths that extend therethrough from a first end to an opposing second end. The carousel is rotatably coupled with the housing so that when the first end of each fluid path is aligned with the inlet port on the housing, the second end of each fluid path is aligned with a corresponding different one of the plurality of outlet ports. A container is fluid coupled to each outlet port by a fluid line. The inlet port can be selectively coupled with a fluid source while a motor can control rotation of the carousel relative to the housing.

15 Claims, 8 Drawing Sheets

(51) Int. Cl.
*F16K 11/085* (2006.01)
*C12M 1/00* (2006.01)
*B65B 3/36* (2006.01)
*B65B 39/00* (2006.01)
*B65B 3/30* (2006.01)

(56) References Cited

U.S. PATENT DOCUMENTS

| | | | | |
|---|---|---|---|---|
| 2,443,333 A * | 6/1948 | Tucker | F15B 11/02 | 137/625.18 |
| 2,485,842 A * | 10/1949 | Pennington | A61M 39/223 | 137/625.19 |
| 2,625,429 A * | 1/1953 | Coles | A01G 25/162 | 122/391 |
| 3,055,404 A * | 9/1962 | Anderson | | 141/144 |
| 3,114,393 A * | 12/1963 | Vlasic | F16K 11/0743 | 137/625.18 |
| 3,131,706 A * | 5/1964 | Harban | C08F 10/00 | 137/15.16 |
| 3,157,201 A * | 11/1964 | Littmann | A61M 39/223 | 137/625.47 |
| 3,678,960 A * | 7/1972 | Leibinsohn | A61M 39/223 | 137/625.47 |
| 3,834,372 A * | 9/1974 | Turney | A61B 5/0215 | 137/625.47 |
| 4,604,093 A * | 8/1986 | Brown | A61M 5/16827 | 137/625.11 |
| 4,630,654 A * | 12/1986 | Kennedy, Jr. | B65B 3/28 | 141/128 |
| 4,712,590 A * | 12/1987 | Gianfilippo | A61J 3/002 | 141/100 |
| 4,850,980 A * | 7/1989 | Lentz | A61M 5/14216 | 137/625.17 |
| 4,900,322 A * | 2/1990 | Adams | | 604/410 |
| 4,946,434 A * | 8/1990 | Plaisted | A61M 1/3693 | 137/625.46 |
| 5,104,387 A * | 4/1992 | Pokorney | A61M 39/223 | 137/625.47 |
| 5,168,905 A * | 12/1992 | Phallen | B65B 3/36 | 141/1 |
| 5,190,524 A * | 3/1993 | Wex | A61M 5/1408 | 604/247 |
| D341,150 S * | 11/1993 | Seegmiller | A61M 5/1408 | 141/106 |
| 5,381,839 A * | 1/1995 | Dowd | B65B 3/30 | 141/237 |
| 5,839,471 A * | 11/1998 | Yang | F16K 11/0712 | 137/625.18 |
| 5,839,486 A * | 11/1998 | Buesing | B65B 59/00 | 141/177 |
| 5,894,011 A * | 4/1999 | Prosl | A61M 1/367 | 210/321.72 |
| 5,941,635 A * | 8/1999 | Stewart | B01F 5/0068 | 366/165.5 |
| 6,655,655 B1 * | 12/2003 | Matkovich | A61M 39/1011 | 251/149.1 |
| 6,908,223 B2 * | 6/2005 | Bibbo et al. | | 366/333 |
| 7,326,355 B2 | 2/2008 | Graetz et al. | | |
| 7,942,170 B2 * | 5/2011 | Gruson | B67C 3/001 | 141/237 |
| 7,967,037 B2 * | 6/2011 | Foster | F04B 15/02 | 141/104 |
| 8,016,003 B2 * | 9/2011 | Bullen | B65B 3/003 | 141/236 |
| 8,789,565 B1 * | 7/2014 | Wicken | A63H 27/10 | 141/237 |
| 8,919,392 B2 * | 12/2014 | Bullen | A63H 27/10 | 141/237 |
| 8,944,296 B2 * | 2/2015 | Vogt | A61B 17/8822 | 222/389 |
| 9,051,066 B1 * | 6/2015 | Malone | A61B 5/155 | |
| 9,073,081 B2 * | 7/2015 | Vogt | A61B 17/8822 | |
| 2002/0117232 A1 * | 8/2002 | Gisper-Sauch | B65B 3/003 | 141/2 |
| 2003/0181850 A1 * | 9/2003 | Diamond | A61M 39/223 | 604/30 |
| 2006/0118472 A1 * | 6/2006 | Schick | B01D 61/18 | 210/198.2 |
| 2008/0090444 A1 * | 4/2008 | Luzbetak | A61M 1/06 | 439/346 |
| 2009/0191631 A1 * | 7/2009 | Bornemann | C12M 23/10 | 435/395 |
| 2009/0202589 A1 * | 8/2009 | Muller | C12M 23/22 | 424/204.1 |
| 2010/0236340 A1 * | 9/2010 | Lee | C12M 37/02 | 73/863.02 |
| 2010/0305507 A1 * | 12/2010 | Duncan | A61M 5/14526 | 604/121 |
| 2010/0319796 A1 * | 12/2010 | Whitaker | F16K 11/085 | 137/625.46 |
| 2011/0011474 A1 * | 1/2011 | Duncan | F16K 11/0853 | 137/625.47 |
| 2011/0264070 A1 * | 10/2011 | Rader | A61M 5/1408 | 604/500 |
| 2011/0310696 A1 | 12/2011 | Goodwin et al. | | |
| 2012/0085461 A1 * | 4/2012 | Coker | G01F 13/00 | 141/237 |
| 2013/0082410 A1 | 4/2013 | Goodwin et al. | | |
| 2013/0240082 A1 * | 9/2013 | Mueller | B65B 3/003 | 141/7 |
| 2014/0053931 A1 * | 2/2014 | Whitaker | F16K 11/0853 | 137/625.17 |
| 2014/0076454 A1 * | 3/2014 | Kjar | C12M 23/40 | 141/1 |
| 2014/0103077 A1 * | 4/2014 | Zumbrum | C12M 23/14 | 222/481 |
| 2014/0213974 A1 * | 7/2014 | Scott | A61M 5/142 | 604/151 |
| 2015/0136272 A1 * | 5/2015 | Brenneis | B65B 37/02 | 141/69 |

OTHER PUBLICATIONS

International Search Report and Written Opinion dated Mar. 21, 2014, issued in PCT Application No. PCT/US2013/055618 filed Aug. 19, 2013.

\* cited by examiner

FLUID MANIFOLD SYSTEM WITH ROTATABLE PORT ASSEMBLY

CROSS-REFERENCE TO RELATED APPLICATIONS

This application claims the benefit of Provisional Application No. 61/701,832, filed Sep. 17, 2012, which is incorporated herein by specific reference.

BACKGROUND OF THE INVENTION

1. The Field of the Invention

The present invention relates to fluid manifold systems that can be used for dispensing fluid from a single fluid source to a plurality of separate containers and, more specifically, to manifold port assemblies of such systems.

2. The Relevant Technology

It is common in the biopharmaceutical industry to dispense sterile fluids, such as media, buffers, and reagents, from a large primary container, where the fluid is prepared, into a plurality of small, disposable bags. The small bags make it easier to transport and use the fluid. The dispensing process is typically accomplished by producing a bag manifold system that includes a plurality of separate discrete bags that are each connected by a section of tubing to a central feed line at spaced apart locations. In turn, the central feed line is connected to a primary container.

Clamps are removably placed at defined points along the feed line and tubing to selectively control feeding of the fluid from the primary container to a select bag. Once one bag is filled, the clamps are manually adjusted to direct the dispensed fluid to a second bag. The process is then repeated until all of the bags are filled. After the bags are filled, the tubing adjacent to each bag is heat sealed closed and then cut so that the filled bags can be removed from the remainder of the manifold.

Although the above manifold system functions, it is cumbersome and labor intensive. For example, most manifold systems typically contain a relatively large number of separate fill bags. These manifold systems are labor intensive to assemble because they include a large number of separate tube sections that must be manually connected together to form the manifold systems. Each connection increases the risk of a leak that would contaminate the sterile fluid. The manifold systems are also unwieldy to package, transport, and position for filling. Likewise, it is labor intensive to monitor the manifold system and adjust the clamps during the filling process.

Accordingly, what is needed in the art are fluid manifold flow systems that have improvements over conventional systems.

BRIEF DESCRIPTION OF THE DRAWINGS

Various embodiments of the present invention will now be discussed with reference to the appended drawings. It is appreciated that these drawings depict only typical embodiments of the invention and are therefore not to be considered limiting of its scope. In the drawings, like numerals designate like elements. Furthermore, multiple instances of an element may each include separate letters appended to the element number. For example two instances of a particular element "20" may be labeled as "20a" and "20b". In that case, the element label may be used without an appended letter (e.g., "20") to generally refer to every instance of the element or any one of the element; while the element label will include an appended letter (e.g., "20a") to refer to a specific instance of the element.

DETAILED DESCRIPTION OF THE PREFERRED EMBODIMENTS

As used in the specification and appended claims, directional terms, such as "top," "bottom," "left," "right," "up," "down," "upper," "lower," "proximal," "distal" and the like are used herein solely to indicate relative directions and are not otherwise intended to limit the scope of the invention or claims.

Figure 1:
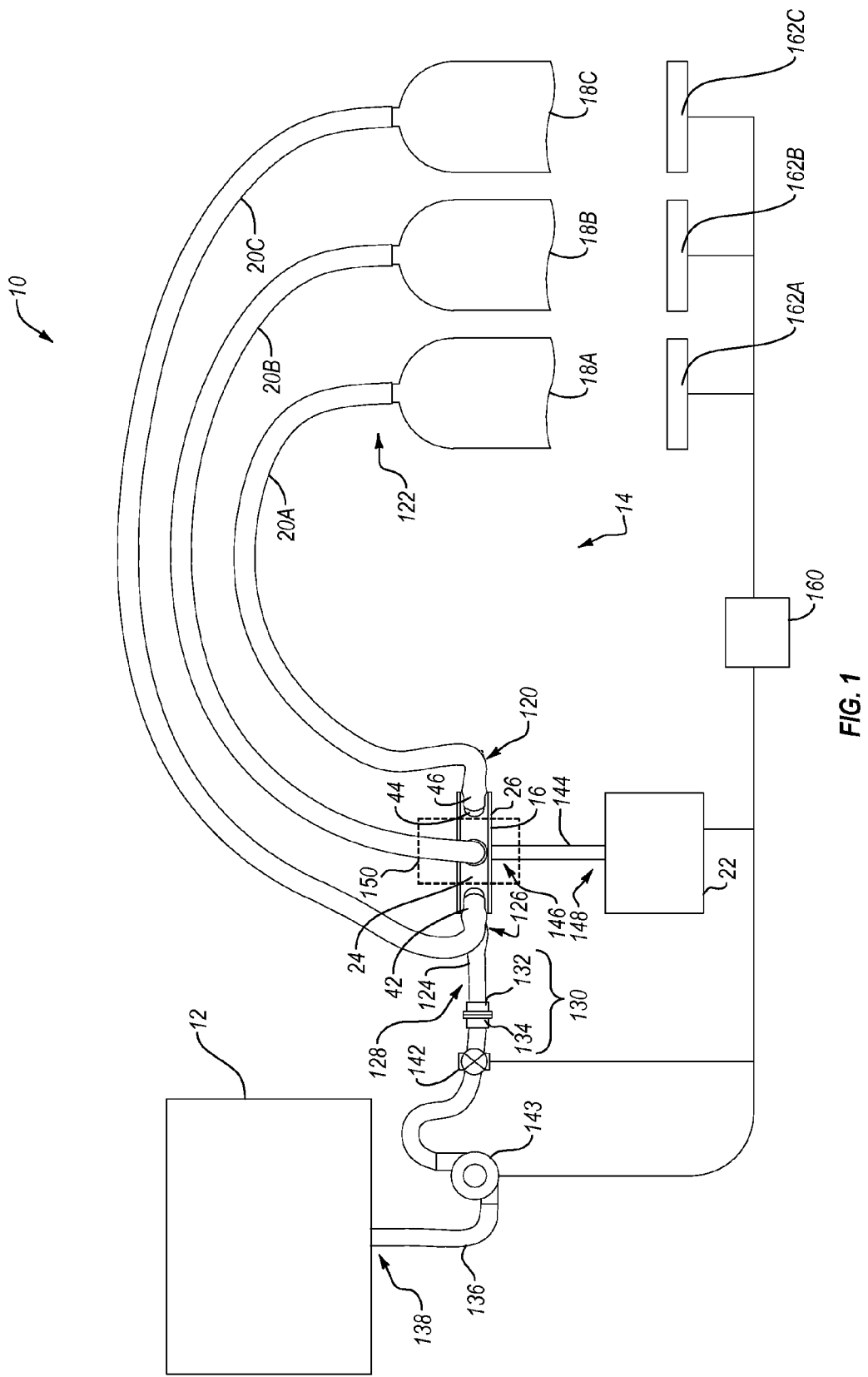
FIG. 1 is a front view of a fluid dispensing system incorporating features of the present invention.

Depicted in FIG. 1 is one embodiment of a fluid dispensing system 10 incorporating features of the present invention. In general, and as will be discussed below in greater detail, fluid dispensing system 10 comprises a fluid source 12 that is coupled with a fluid manifold system 14. Fluid manifold system 14 comprises a manifold port assembly 16 having a plurality of containers 18 coupled thereto by a plurality of fluid lines 20. A motor 22 couples with manifold port assembly 16 to control selective filling of discrete containers 18. The different components of fluid dispensing system 10 will now be discussed in greater detail.

Figure 2:
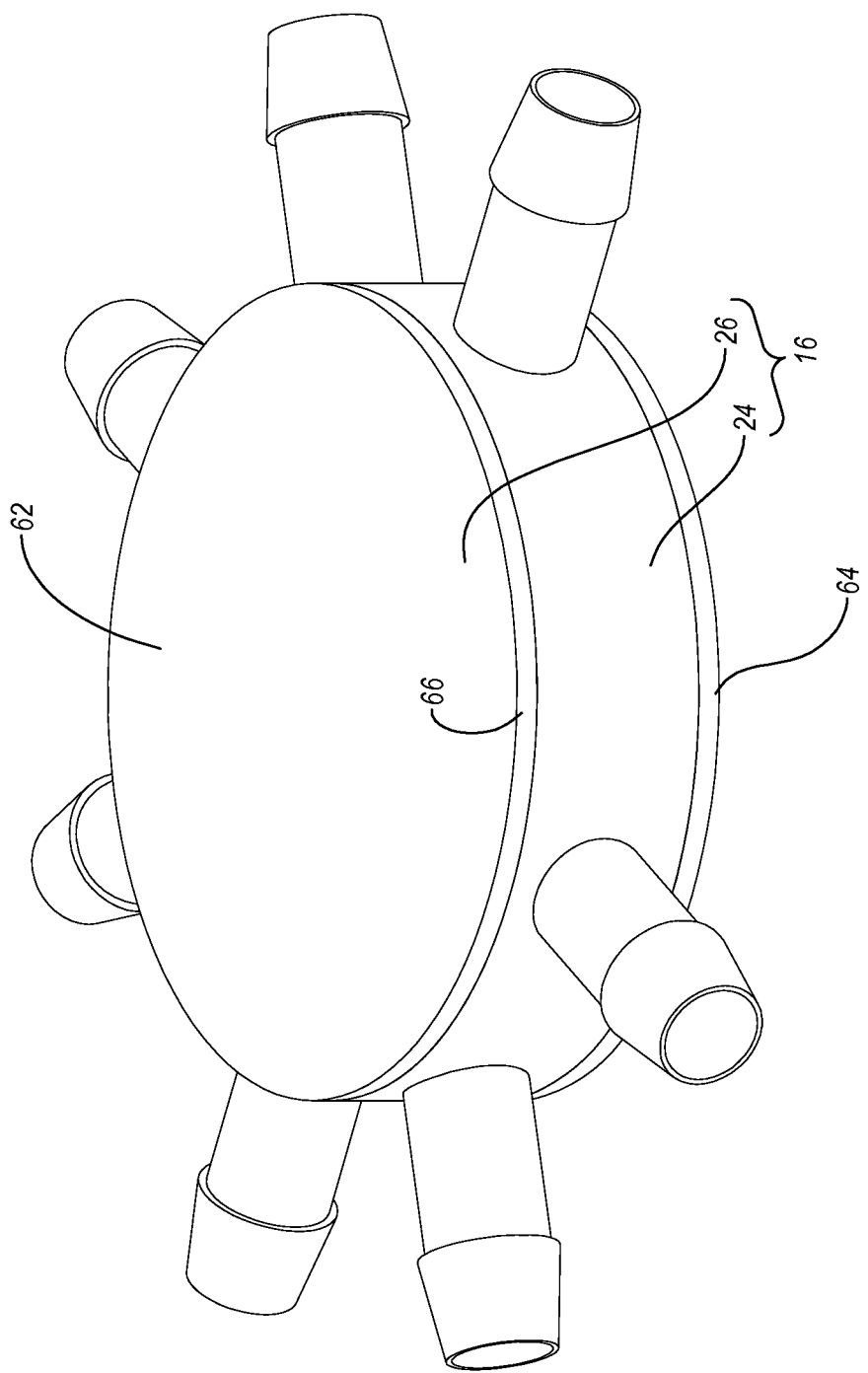
FIG. 2 is a top perspective view of a manifold port assembly shown in FIG. 1.
Figure 3:
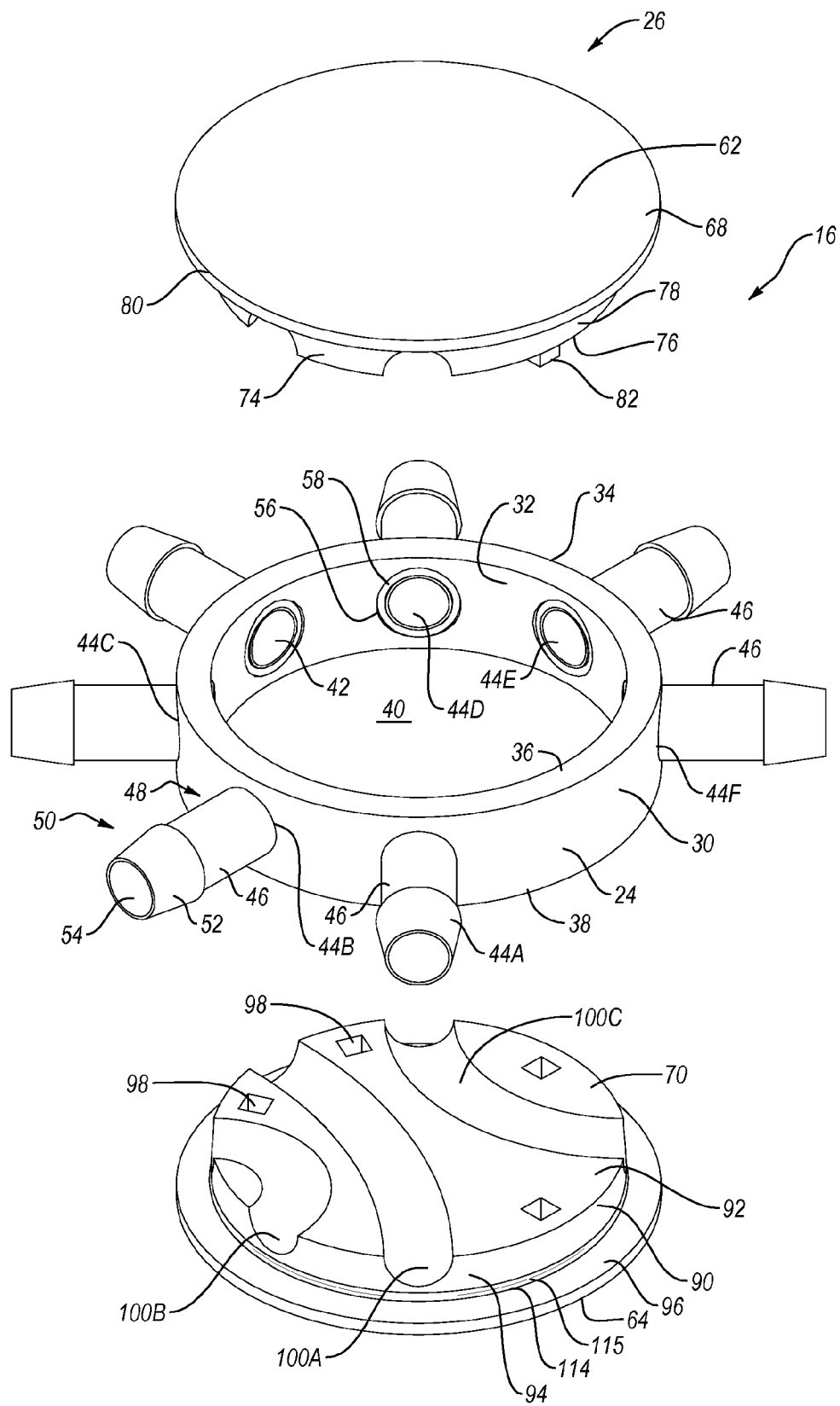
FIG. 3 is an exploded perspective view of the manifold port assembly shown in FIG. 2.
Figure 8:
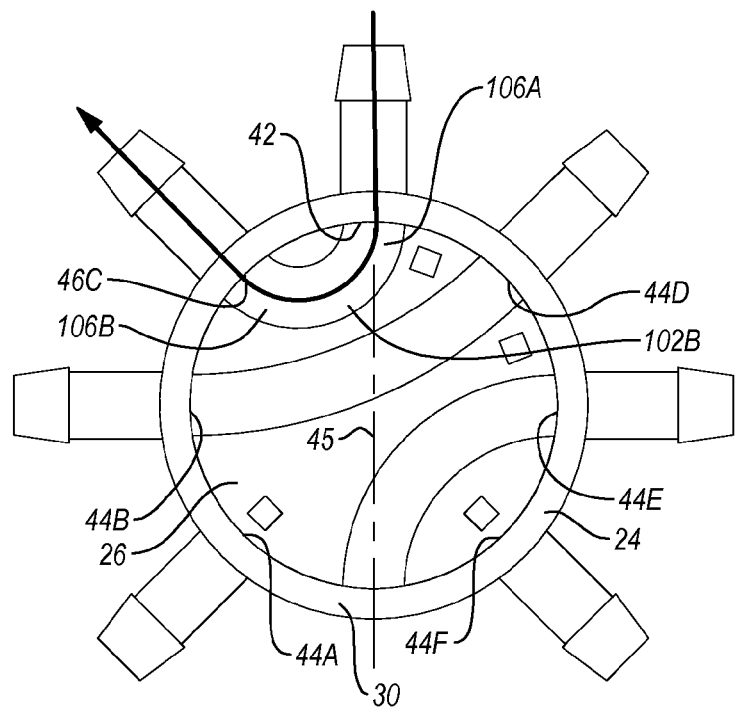
FIG. 8 is a top plan view of the manifold port assembly shown in FIG. 6 with the carousel in a third position.

FIG. 2 is a perspective view of manifold port assembly 16. As shown therein, manifold port assembly 16 comprises an annular housing 24 having a carousel 26 rotatably coupled thereto. More specifically, as depicted in FIG. 3, housing 24 comprises an encircling sidewall 30 having an interior surface 32 and an exterior surface 34 that extend between a top edge 36 and an opposing bottom edge 38. Interior surface 32 is substantially circular so as to encircle and partially bound a compartment 40. Exterior surface 34 is also shown as being circular but can be a variety of alternative configurations. For example, exterior surface 34 can have a polygonal, oval, irregular, or other configuration. Extending through sidewall 30 from interior surface 32 to exterior surface 34 is an inlet port 42 and a plurality of radially spaced apart outlet ports 44A-44F. As depicted in FIG. 8, a central longitudinal axis 45 is shown extending through inlet port 42. Although not required, outlet ports 44A-44F are shown as being formed in pairs with each pair being symmetrically formed on sidewall 30 on opposing sides of longitudinal axis 45. For example, outlet ports 44A and 44F are symmetrically formed on opposing sides of axis 45. Likewise, outlet ports 44B, 44E and 44C, 44D are symmetrically paired on sidewall 30.

Returning to FIG. 3, outwardly projecting from each port 42 and 44 is a corresponding tubular port stem 46. Each port stem 46 has a first end 48 secured to sidewall 30 so as to be aligned with a corresponding port 42, 44 and has an opposing second end 50 that is freely disposed. An annular barb 52 encircles and radially outwardly projects from second end 50 of each port stem 46. Each port stem 46 bounds a passageway 54 that communicates with a corresponding port 42, 44. As will be discussed below in greater detail, an annular groove 56 is formed on interior surface 32 of sidewall 30 and encircles each of ports 42, 44. An O-ring 58 is securely received within each annular groove 56.

Figure 4:
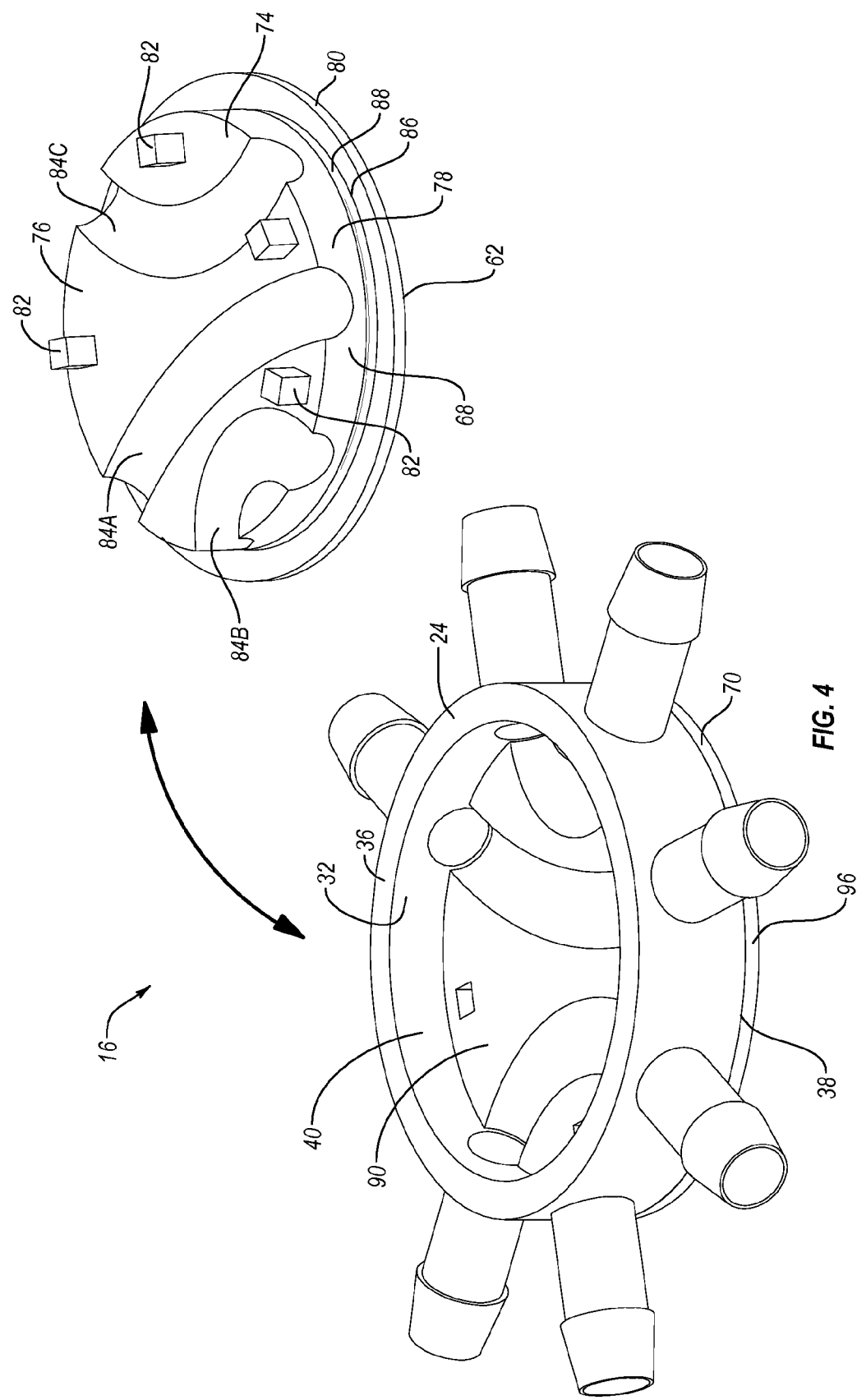
FIG. 4 is a partially exploded view of the manifold port assembly shown in FIG. 2.

As depicted in FIG. 2, in general carousel 26 has a top face 62 and an opposing bottom face 64 with an encircling side surface 66 extending therebetween. More specifically, as depicted in FIG. 3, carousel 26 comprises an upper body 68 and a lower body 70 that are selectively coupled together. As depicted in FIGS. 3 and 4, upper body 68 comprises a central base 74 having a generally cylindrical configuration that includes an inside face 76, top face 62 and an encircling side face 78 that extends therebetween. Side face 78 has a circular transverse cross section. An annular flange 80 encircles and radially outwardly projects from side face 78 of base 74 at top face 62. Base 74 is configured so that it can be rotatably received within compartment 40 of housing 24. When base 74 is received within compartment 40, flange 80 extends over top edge 36 of housing 24 to assist in maintaining carousel 26 coupled with housing 24. An annular groove 86 is recessed on side face 78 so as to encircle side face 78. An O-ring 88 or other seal is received within groove 86. Base 74 is configured so that when base 74 is rotatably received with compartment 40, O-ring 88 forms a liquid tight seal between base 74 and inside face 32 of housing 24. In an alternative embodiment, groove 86 and O-ring 88 can be disposed on inside face 32 of housing 24.

Outwardly projecting from inside face 76 are a plurality of spaced apart mounting projections 82. Recessed on inside face 76 are three spaced apart channels 84A-C. Each channel 84 extends in a curved arch that passes through side face 78 at a first location and a spaced apart second location. The arch of each channel 84 has a different configuration. Although each channel 84 is shown as having a semi-circular transverse cross section, other configurations such as semi-polygonal or semi-elliptical can also be used.

As shown in FIG. 3, lower body 70 has a configuration similar to that of upper body 68. Specifically, lower body 70 includes a base 90 having an inside face 92, bottom face 64 and an encircling side face 94 that extends therebetween. A groove 114 and O-ring 115 are disposed on side face 94. An annular flange 96 encircles and radially outwardly projects from side face 94 at bottom face 64. Inside face 92 has mounting pockets 98 that are complimentary in location and configuration to mounting projections 82. As such, bodies 68 and 70 can be secured together by advancing projections 82 into pockets 98. Bodies 68 and 70 can be held together by press-fit connection or through the use of an adhesive. Other fastening techniques can also be used to hold together bodies 68 and 70. For example, bodies 68 and 70 can be screwed, bolted, or snap-fit together.

Figure 6:
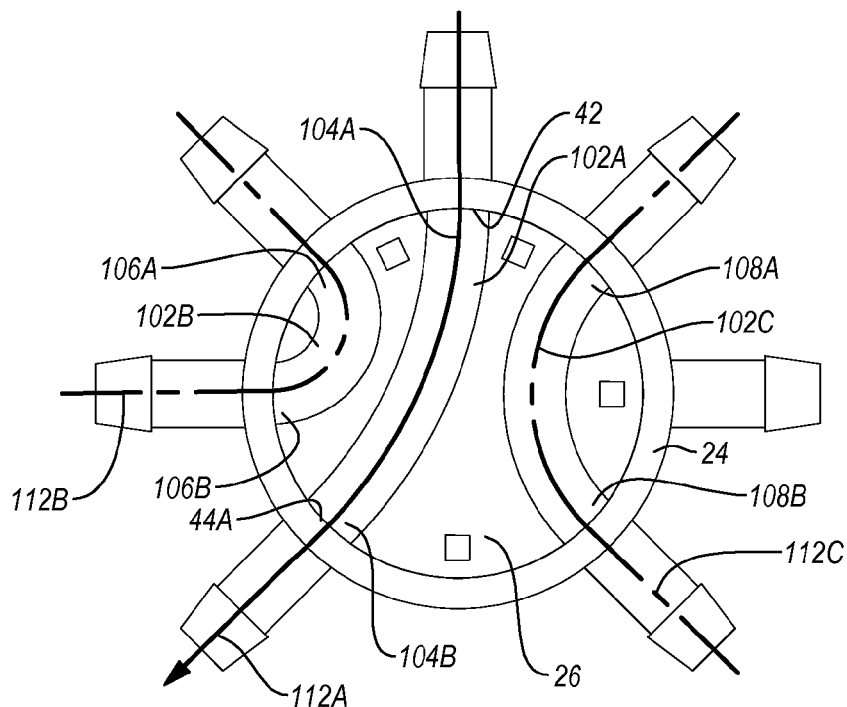
FIG. 6 is a top plan view of the manifold port assembly shown in FIG. 2 with the upper body removed and the carousel thereof in a first position.

Channels 100A-C are recessed on inside face 92 of base 90 and are the mirror image of channels 84A-C. Accordingly, when bodies 68 and 70 are mated together, channels 84 and 100 line up to form fluid paths 102A, 102B, and 102C as shown in FIG. 6. Fluid path 102A has a first end 104A and an opposing second end 104B. Similarly, fluid path 102B has a first end 106A and an opposing second end 106B while fluid path 102C has a first end 108A and an opposing second end 108B. Although each fluid path 102 is shown as having a circular transverse cross section, other configurations such as polygonal or elliptical can also be used.

To assemble manifold port assembly 16, bases 74 and 90 are received within compartment 40 from opposing sides of housing 24. Bases 74 and 90 are secured together within compartment 40 so as to form and bound fluid paths 102A-C therebetween. Flanges 80 and 96 project over opposing edges 36 and 38 of housing 24. In this configuration, carousel 26 can rotate relative to housing 24 but flanges 80 and 96 precluded carousel 26 from falling out of compartment 40.

Figure 7:
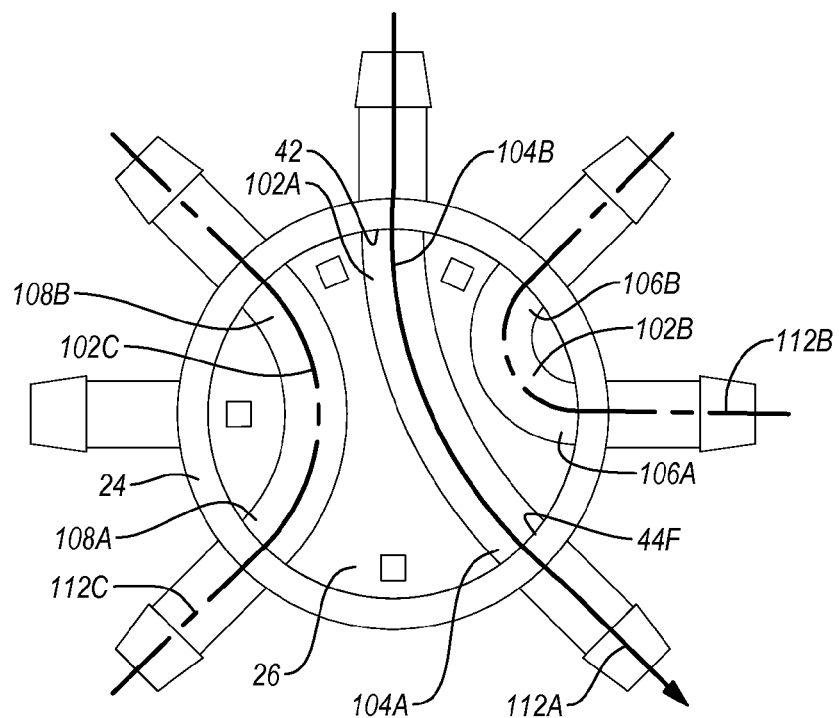
FIG. 7 is a top plan view of the manifold port assembly shown in FIG. 6 with the carousel in a second position.
Figure 9:
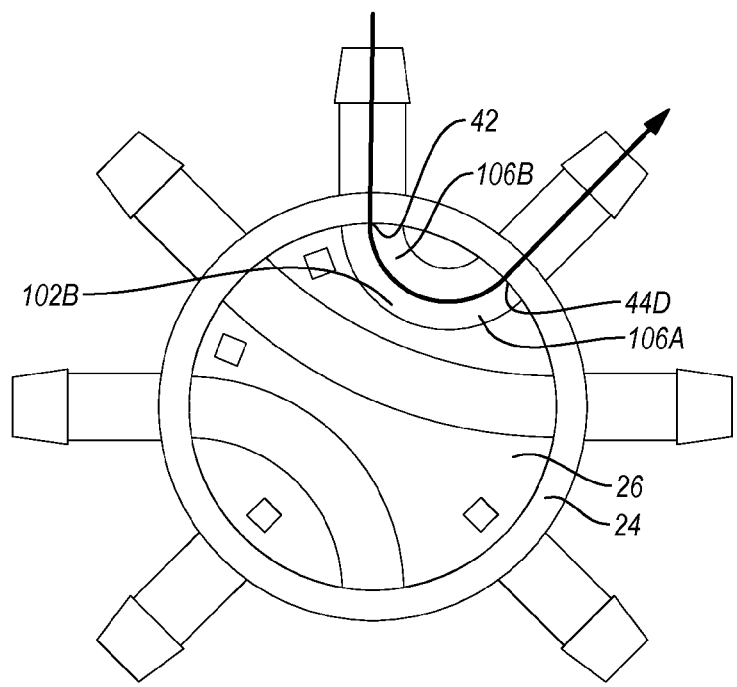
FIG. 9 is a top plan view of the manifold port assembly shown in FIG. 6 with the carousel in a fourth position.
Figure 10:
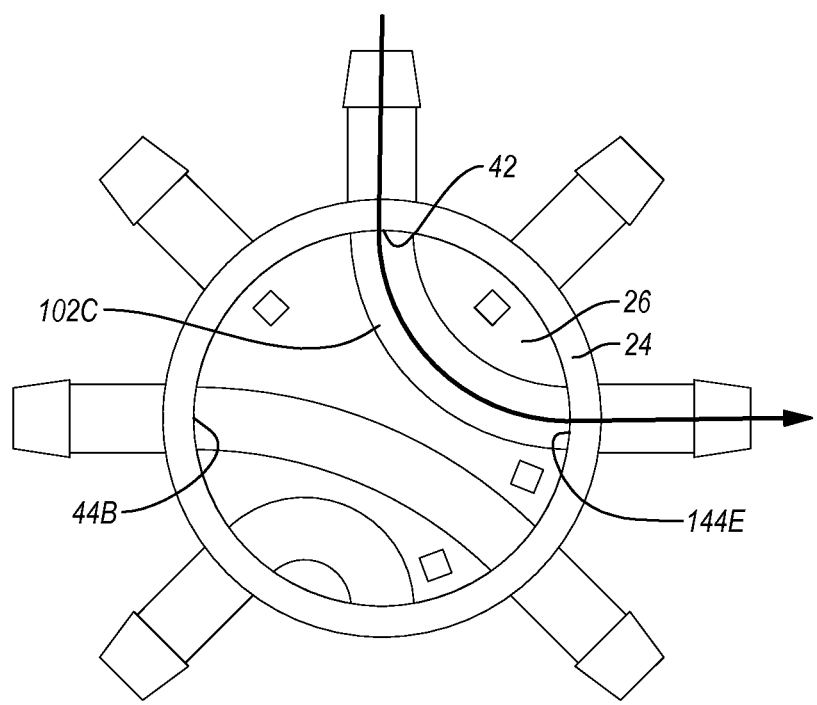
FIG. 10 is a top plan view of the manifold port assembly shown in FIG. 6 with the carousel in a fifth position.

Returning to FIG. 6, each fluid path 102A-C has a corresponding central longitudinal axis 112A-C, respectively. Each fluid path 102 and corresponding longitudinal axis 112 have an arched curvature with each curvature being different. The curvatures are configured so that each fluid path 102 can align inlet port 42 with one of the pairs of complementary outlet ports 44 as discussed above. For example, as shown in FIG. 6, carousel 26 is rotated relative to housing 24 so that inlet port 42 is aligned with first end 104A of fluid path 102A and second end 104B of fluid path 102A is aligned with outlet port 44A. In FIG. 7, however, carousel 26 has been rotated so that second end 104B of fluid path 102A is aligned with inlet port 42 and first end 104A of fluid path 102 is aligned with outlet port 44F. Similarly, in FIG. 8 carousel 26 has been rotated relative to housing 24 so that first end 106A of fluid path 102B is aligned with inlet port 42 while opposing second end 106B is aligned with outlet port 44C. By again rotating carousel 26, second end 106B of fluid path 102B can be aligned with inlet port 42 while first end 106A is aligned with outlet port 44D as shown in FIG. 9. Likewise, carousel 26 can be rotated so that fluid path 102C provides fluid communication between inlet port 42 and outlet port 44E as shown in FIG. 10 and between inlet port 42 and outlet port 44B. In each of the different rotated positions, O-rings 58 (FIG. 3) effect a sealed engagement between the port 40, 42 and the end of the corresponding fluid path 102.

In the depicted embodiment, fluid paths 102 are shown as having a smooth arched curvature and a circular cross section so as to minimize turbulence and sheering forces that could be applied to cells or microorganisms within the fluid being transferred. In other embodiments, however, fluid paths 102 can be formed with one or more discrete angles as opposed to a continuous arch.

Figure 5:
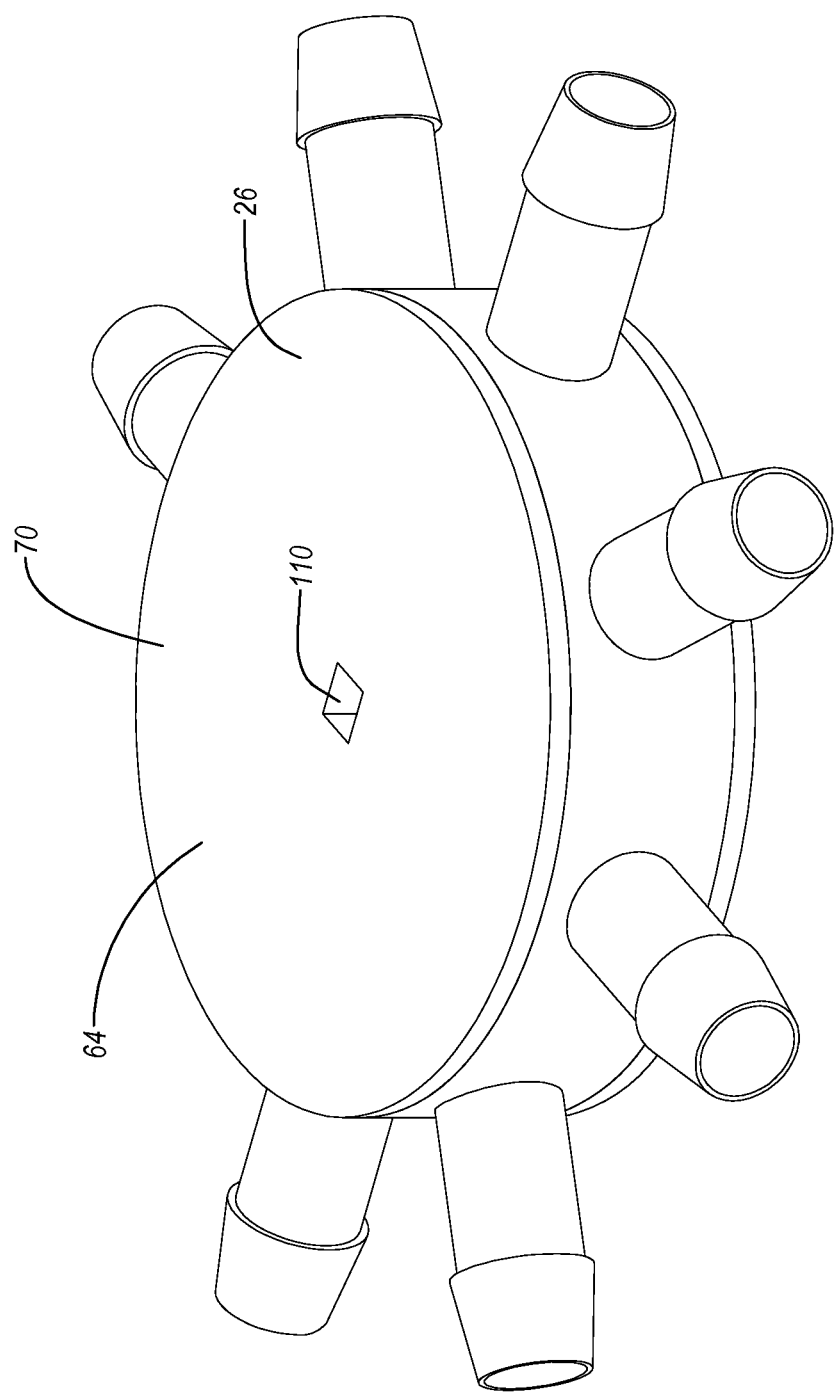
FIG. 5 is a bottom perspective view of the manifold port assembly shown in FIG. 2.

In one embodiment on the present invention, means are provided for coupling a drive shaft to carousel 26 for select rotation of carousel 26 relative to housing 24. By way of example and not by limitation, depicted in FIG. 5 is a socket 110 that is centrally formed on bottom face 64 of carousel 26. Socket 110 is depicted as having a square transverse cross sectional configuration so that it can receive and engage the end of a drive shaft having a complementary configuration. Once coupled together, rotation of the drive shaft facilitates rotation of carousel 26. In alternative embodiments, socket 110 can have a polygonal, elliptical, irregular, or other non-circular transverse cross sectional configuration that can engage the end of a drive shaft. In still other embodiments of the means for coupling, socket 110 can be replaced with a stem outwardly projecting from bottom face 64 and having a polygonal, elliptical, irregular, or other non-circular transverse cross sectional configuration. A socket disposed on the end of a drive shaft can engage the stem for selective rotation of carousel 26. In still other embodiments, it is appreciated that socket 110 can be replaced with a threaded opening, fasteners, clamps, and any other type of conventional connector that can be used for connecting a drive shaft to carousel 26.

It is appreciated that the depicted manifold port assembly 16 is only one embodiment of how the port assembly can be configured and that in addition to the alternative embodiments as previously discussed, manifold port assembly 16 can have a variety of other configurations. By way of example and not by limitation, in the depicted embodiment port stems 46 (FIG. 3) are either integrally formed as a unitary structure with sidewall 30 or are rigidly fixed to sidewall 30 such as by welding or an adhesive. In alternative embodiments, ports stems 46 can be replaced with a socket or other type of connector to which a fluid line can be selectively coupled. Likewise, in contrast to having sidewall 30 of housing 24 form a continuous circle, interior surface 32 of sidewall 30 can be C-shaped or U-shaped and thus not a continuous circle. Furthermore, bases 74 and 90 of carousel 26 can be integrally formed as a single unitary structure having fluid paths 102 extending therethrough. In this embodiment, one of flanges 80 or 96 can be removably attached to the remainder of carousel 26 for selective retention on housing 24. In this embodiment, O-rings 58 could be secured on carousel 26 as opposed to housing 24 so as to circle the opposing openings of each fluid path 102. It is also appreciated that flanges 80 and 96 need not completely encircle carousel 26 and that the flanges can be replaced with other structures that are either permanently or removably attached to the central base portions for retention to housing 24.

In still other embodiments, it is appreciated that manifold port assembly 16 can be formed with any desired number of outlet ports 44 and corresponding fluid paths 102. For example, carousel 26 can be formed with one, two, four, five, six or more fluid paths 102. In contrast to being arched, one or more of fluid paths 102 can be linear or have other configurations as long as the opposing ends are properly positioned. Fluid paths 102 can be configured to couple with only one outlet port 44 or with a pair of outlet ports 44 as depicted and discussed above. As such, housing 24 can be formed with two, three, four, five, seven, eight, nine, ten, or more outlet ports 44.

Although manifold port assembly 16 can be made of any sterilizable material, manifold port assembly 16 is typically designed as a disposable, single use item. It is likewise desirable to form manifold port assembly 16 out of a material having a relatively low coefficient of friction so that smooth rotation can be formed between carousel 26 and housing 24. By way of example and not by limitation, manifold port assembly 16 is typically comprised of a polymeric material such as polypropylene. Other materials can also be used.

As previously discussed, flow manifold system 14 comprises manifold port assembly 16 coupled with containers 18 by fluid lines 20 as depicted in FIG. 1. Containers 18 can comprise rigid containers, semi-rigid containers (such as plastic bottles), or collapsible bags. The collapsible bags can be either two dimensional pillow style bags or three dimensional bags that are each formed from one or more polymeric sheets that are welded together. The polymeric sheets can be comprised of a flexible, water impermeable material such as low-density polyethylene or other polymeric sheets having a thickness in a range between about 0.1 mm to about 5 mm with about 0.2 mm to about 2 mm being more common. Other thicknesses can also be used. The material can be comprised of a single ply material or can comprise two or more layers which are either sealed together or separated to form a double wall container. Where the layers are sealed together, the material can comprise a laminated or extruded material. The laminated material comprises two or more separately formed layers that are subsequently secured together by an adhesive. Examples of extruded material that can be used in the present invention include the HyQ CX3-9 and HyQ CX5-14 films available from HyClone Laboratories, Inc. out of Logan, Utah. The material can be approved for direct contact with living cells and be capable of maintaining a solution sterile. In such an embodiment, the material can also be sterilizable such as by ionizing radiation. The collapsible bags are typically designed to hold a volume in a range between about 10 liters to about 200 liters with about 20 liters to about 100 liters being more common. Other volumes can also be used.

Fluid lines 20 typically comprise flexible tubing that is comprised of a polymeric material. Alternatively, fluid lines 20 can be rigid or semi-rigid. Each fluid line 20 has a first end 120 that is received over a corresponding port stem 46 so as to be in sealed fluid communication with a corresponding outlet port 44. Each fluid line 20 also has an opposing second end 122 that is fluid coupled with a corresponding container 18 using conventional methods.

Flow manifold system 14 also typically comprises a fluid line 124 having a first end 126 coupled with the port stem 46 aligned with inlet port 42. Fluid line 124 also has an opposing second end 128 coupled with a connector 130. In the embodiment depicted, connector 130 comprises an aseptic connector such as the KLEENPACK® sterile connector produced by the Pall Corporation. One embodiment of the KLEENPACK® sterile connector is disclosed in U.S. Pat. No. 6,655,655 which is incorporated herein by specific reference. Aseptic connectors enable the formation of sterile fluid connections between two fluid lines in a non-sterile environment. Aseptic connector 130 comprises a first connector portion 132 that is fluid coupled with second end 128 of fluid line 124 and a second connector portion 134 that is connected to an end of a fluid line 136 extending from fluid source 12. Portions 132 and 134, which can comprise complementary male and female connectors, can be selectively connected together to form a sterile fluid connection therebetween.

First connector portion 132 is sealed closed when connected to fluid line 124 and remains so until used. As a result, once fluid manifold system 14 is assembled, the area within fluid manifold system 14 is sealed closed. This enables fluid manifold system 14 to be fully assembled and then sterilized prior to use as a complete assembly. In alternative embodiments, connector 130 need not be an aseptic connector but can be any form of a non-aseptic connector that is sealed closed prior to use. As the time of use, the connection is made within a sterile environment to form a sterile fluid connection.

Continuing with FIG. 1, fluid source 12 can comprise a rigid container such as a stainless steel tank, a semi-rigid container such as a plastic barrel, or can comprise a collapsible bag that is housed within a rigid support housing. The collapsible bag for fluid source 12 can comprise a two or three dimensional bag formed from the same materials and process as discussed above with regard to containers 18. The collapsible bag for fluid source 12 can typically hold a volume of fluid in a range between about 50 liters to about 10,000 liters and can typically hold more than 400 liters, 900 liters or 1,400 liters. Fluid source 12 can comprise a bioreactor, fermentor, mixer or just a container. The container for fluid source 12 can be a closed sterile container or an open non-sterile container. Examples of fluid mixing systems that can be used as fluid source 12 are disclosed in US Patent Publication No. 2011/0310696 which is incorporated herein by specific reference.

Fluid line 136 has a first end 138 that is fluid coupled with fluid source 12. First end 138 is typically coupled to the floor or lower end of the container forming fluid source 12 so that the fluid can flow under gravitational force through fluid line 138 and into flow manifold system 14. A valve 142, such as a clamp or other type of conventional manual or electrical valve, can be coupled with fluid line 136 to control the flow of fluid therethrough. In an alternative embodiment, first end 138 of fluid line can extend into the container of fluid source 12 through an upper end of the container. In this embodiment, a pump 143 can be used to dispense fluid out of fluid source 12. The fluid within fluid source 12 can be any sterile or non-sterile fluids. Examples of common fluids that can be used in the biopharmaceutical industry include media, buffers, reagents, cell or microorganism cultures, deionized water and the like. However, the present invention can also be used with other fluids such as chemicals, food products, and other processed fluids.

Also depicted in FIG. 1 is a drive shaft 144 having a first end 146 coupled to carousel 26 of manifold port assembly 16. The engagement can be by way of socket 110 as previously discussed with regard to FIG. 5. Drive shaft 144 also has an opposing second end 148 that couples with motor 22. Motor 22 can comprise a stepper motor or any other type of motor or drive mechanism that can be used for selectively rotating drive shaft 144 which in turn rotates carousel 26.

Finally, FIG. 1 also shows a support identified by dash lines 150. Support 150 is designed to retain housing 24 in a fixed position while carousel 26 is rotated relative thereto. Support 150 can comprise a clamp, fastener, or any other type of structure that can engage with housing 24 for retaining housing 24 relative to carousel 26. Support 150 would typically be mounted on a table, stand, or other movable or fixed structure.

During operation, either before or after the fluid has been prepared within fluid source 12, fluid manifold system 14 is fluid coupled with fluid source 12 by coupling first connector portion 132 with second connector portion 134. Drive shaft 144 is also coupled with carousel 26 and housing 24 is secured to support 150. In this configuration, motor 22 can be activated to rotate carousel 26 so that inlet port 42 is fluid coupled with an outlet port 44 that is fluid coupled with a corresponding container 18. Fluid from fluid source 12 can then pass through fluid line 136 and the corresponding open channel formed in fluid manifold system 16 so that the fluid can fill the corresponding container 18. Once the container 18 is filled to a desired level, carousel 26 can be rotated so that inlet port 42 is align with a second outlet port 44 which is fluid coupled with a second container 18. Valve 142 can be temporarily closed or pump 143 can be temporarily stopped while carousel 26 is being rotated to the second position. This process can then be repeated until all of containers 18 are filled. Fluid lines 20 can then be heat sealed at a location close of containers 18 and then cut so as to permit the removal of containers 18.

Containers 18 can be filled to a desired volume by visual inspection. Alternatively, the filling process can be automated by filling a container 18 at a specific flow rate for a specific time. In another automated process, containers 18 can be weighed during filling with the fluid flow stopping once a container 18 has achieved a predetermined weight. For example, an electronic control unit 160 can be electrically coupled with motor 122, valve 144 and/or pump 143, and a plurality of scales 162A-C on which containers 18A-C are resting, respectively. The electronic control unit 160 automatically controls the opening of a fluid path from fluid source 12 to an identified container 18 by controlling motor 22 which controls the movement of carousel 26. Once a corresponding scale 162 senses that a container 18 has been filled to a desired weight, electronic control unit 160 stops the fluid flow, such as by closing valve 142, and then rotates carousel 26 for filling the next container 18 with fluid. The process is then repeated until all of the containers 18 are filled.

The inventive fluid manifold system 14 achieves a number of benefits over the known prior art systems. For example, by using manifold port assembly 16, the size, complexity, number of parts, and number of fluid connections of the manifold system is reduced relative to conventional manifold systems. As such, the inventive manifold system is easier to produce, easier to manipulate, requires less space for packaging and storing and there is a lower chance for leaking and fluid contamination. Furthermore, in contrast to having to manually clamp off separate lines to selectively fill different containers, manifold port assembly 16 permits automated filling of the separate containers. As such, the inventive system is less labor intensive to build and less labor intensive to operate.

The present invention may be embodied in other specific forms without departing from its spirit or essential characteristics. The described embodiments are to be considered in all respects only as illustrative and not restrictive. The scope of the invention is, therefore, indicated by the appended claims rather than by the foregoing description. All changes which come within the meaning and range of equivalency of the claims are to be embraced within their scope.

What is claimed is:

1. A manifold port assembly comprising:
   a housing bounding a compartment and having an inlet port and six outlet ports formed thereon and communicating with the compartment; and
   a carousel bounding three spaced apart fluid paths that extend therethrough from a corresponding first end to an opposing corresponding second end, at least a portion of each fluid path being spaced apart from the housing and being radially enclosed by the carousel, the carousel being rotatably disposed within the compartment of the housing so that when the first end or the second end of each fluid path is aligned with the inlet port on the housing, the other of the first end or second end of each fluid path is aligned with a corresponding different one of each of the six outlet ports, wherein each fluid path has a central longitudinal axis extending along the length thereof that is arched, each arch having a different curvature.

2. The manifold port assembly as recited in claim 1, wherein the housing comprises an annular sidewall that encircles the compartment, the inlet port and the plurality of outlet port each extending through the sidewall at spaced apart locations.

3. The manifold port assembly as recited in claim 2, wherein the housing further comprises a plurality of tubular port stems, each port stem being coupled with a corresponding outlet port so as to outwardly project from the sidewall.

4. The manifold port assembly as recited in claim 1, wherein the carousel comprises an upper body and a lower body that are coupled together and that bound the plurality of fluid paths therebetween.

5. The manifold port assembly as recited in claim 1, further comprising means for coupling a drive shaft to carousel for selective rotation of the carousel relative to the housing.

6. The manifold port assembly as recited in claim 1, wherein the means for coupling the drive shaft to carousel comprises a driver socket formed on the carousel.

7. A fluid dispensing system comprising:
a manifold port assembly comprising:
a housing having an inlet port and a plurality of outlet ports formed thereon; and
a carousel bounding a plurality of spaced apart fluid paths that each extend therethrough from a corresponding first end to an opposing corresponding second end, at least a portion of each fluid path being spaced apart from the housing and being radially enclosed by the carousel, the carousel being rotatably coupled with the housing so that when the first end of each fluid path is aligned with the inlet port on the housing, the second end of each fluid path is aligned with a corresponding different one of the plurality of outlet ports;
a fluid source;
a primary fluid line extending from the fluid source to the inlet port of the manifold port assembly;
a plurality of containers;
a plurality of secondary fluid lines, each secondary fluid line extending from a select one of the outlet ports of the manifold port assembly to a select one of the plurality of containers; and
a motor coupled with the carousel for rotating the carousel relative to the housing.

8. The fluid dispensing system as recited in claim 7, wherein the manifold port assembly, primary fluid line, plurality of containers, and plurality of secondary fluid lines are sterilized as an assembled unit.

9. The fluid dispensing system as recited in claim 7, further comprising an aseptic connector securing the primary fluid line to the fluid source.

10. The fluid dispensing system as recited in claim 7, wherein the fluid source comprises a bioreactor or fermentor.

11. The fluid dispensing system as recited in claim 7, further comprising a sterile fluid housed within the fluid source.

12. The fluid dispensing system as recited in claim 7, wherein each of the plurality of containers comprises a collapsible bag.

13. The fluid dispensing system as recited in claim 7, further comprising:

a plurality of weight scales, each of the plurality of containers being supported on a separate one of the weight scales; and
an electronic control unit being electrically coupled with the motor and the scales.

14. A method of dispensing fluid, the method comprising:
dispensing a first volume of fluid from a fluid source so that fluid flows from a primary fluid line coupled to the fluid source, through a manifold port assembly coupled to the primary fluid line, through a first secondary fluid line that is coupled to the manifold port assembly, and into a first container, the manifold port assembly comprising:
a housing having an inlet port and a plurality of outlet ports formed thereon; and
a carousel bounding a plurality of spaced apart fluid paths that each extend therethrough from a corresponding first end to an opposing corresponding second end, the carousel being rotatably coupled with the housing so that when the first end of each fluid path is aligned with the inlet port on the housing, the second end of each fluid path is aligned with a corresponding different one of the plurality of outlet ports;
rotating the carousel of the manifold port assembly to a second position;
dispensing a second volume of fluid from the fluid source so that fluid flows from the primary fluid line coupled to the fluid source, through the manifold port assembly coupled to the primary fluid line, through a second secondary fluid line that is coupled to the manifold port assembly, and into a second container;
rotating the carousel of the manifold port assembly to a third position; and
dispensing a third volume of fluid from the fluid source so that fluid flows from the primary fluid line coupled to the fluid source, through the manifold port assembly coupled to the primary fluid line, through a third secondary fluid line that is coupled to the manifold port assembly, and into a second container,
wherein each container is disposed on a weight scale and the carousel is automatically rotated to the second position when the weight of the fluid on the first scale reaches a predetermined value.

15. The method as recited in claim 14, wherein the fluid comprises a sterile fluid.

* * * * *